(12) United States Patent
Gelbart et al.

(10) Patent No.: US 7,749,249 B2
(45) Date of Patent: Jul. 6, 2010

(54) METHOD AND DEVICE FOR CLOSING HOLES IN TISSUE

(75) Inventors: Daniel Gelbart, Vancouver (CA); Samuel Victor Lichtenstein, Vancouver (CA)

(73) Assignee: Kardium Inc., Vancouver (CA)

( * ) Notice: Subject to any disclaimer, the term of this patent is extended or adjusted under 35 U.S.C. 154(b) by 254 days.

(21) Appl. No.: 11/436,585

(22) Filed: May 19, 2006

(65) Prior Publication Data

US 2007/0198058 A1    Aug. 23, 2007

Related U.S. Application Data

(63) Continuation-in-part of application No. 11/357,011, filed on Feb. 21, 2006, now abandoned.

(51) Int. Cl.
*A61B 17/50* (2006.01)
(52) U.S. Cl. ..................................................... 606/216
(58) Field of Classification Search ................ 606/213, 606/216, 142–143
See application file for complete search history.

(56) References Cited

U.S. PATENT DOCUMENTS

| | | | |
|---|---|---|---|
| 4,114,202 A | 9/1978 | Roy et al. ........................ 3/1.5 |
| 4,164,046 A | 8/1979 | Cooley ............................ 3/1.5 |
| 4,240,441 A | 12/1980 | Khalil .......................... 128/692 |
| 4,263,680 A | 4/1981 | Reul et al. ...................... 3/1.5 |
| 4,490,859 A | 1/1985 | Black et al. ..................... 3/1.5 |
| 4,543,090 A | 9/1985 | McCoy ........................ 604/95 |
| 4,794,912 A | 1/1989 | Lia ................................ 128/4 |
| 4,850,957 A | 7/1989 | Summers ...................... 604/22 |
| 4,890,602 A | 1/1990 | Hake .............................. 128/4 |
| 4,890,612 A | 1/1990 | Kensey |
| 4,893,613 A | 1/1990 | Hake .............................. 128/4 |
| 4,921,499 A | 5/1990 | Hoffman et al. .............. 623/16 |
| 5,021,059 A | 6/1991 | Kensey et al. |
| 5,047,047 A * | 9/1991 | Yoon .......................... 606/216 |
| 5,100,418 A | 3/1992 | Yoon et al. |
| 5,104,399 A | 4/1992 | Lazarus |
| 5,122,137 A | 6/1992 | Lennox ........................ 606/40 |
| 5,156,609 A * | 10/1992 | Nakao et al. ................. 606/142 |
| 5,192,314 A | 3/1993 | Daskalakis ..................... 623/3 |
| 5,258,000 A | 11/1993 | Gianturco |
| 5,312,435 A | 5/1994 | Nash |

(Continued)

FOREIGN PATENT DOCUMENTS

WO        90/15582        12/1990

(Continued)

OTHER PUBLICATIONS

CARDIOSEAL product brochure from website of NMT-Medical (www.nmtmedical.com), May 13, 2006, attached page.

(Continued)

*Primary Examiner*—(Jackie) Tan-Uyen T Ho
*Assistant Examiner*—Son Dang
(74) *Attorney, Agent, or Firm*—Seed IP Law Group PLLC

(57) ABSTRACT

A device for closing holes in tissue is delivered via a catheter to the inside of a body lumen such as a heart. An elastic barbed clip is expanded, pulled into the tissue and released, pulling the tissue with it. The operation is fully reversible.

21 Claims, 9 Drawing Sheets

U.S. PATENT DOCUMENTS

| | | | |
|---|---|---|---|
| 5,320,632 A | 6/1994 | Heidmueller | |
| 5,364,408 A | 11/1994 | Gordon | |
| 5,366,443 A | 11/1994 | Eggers et al. | 604/114 |
| 5,366,459 A | 11/1994 | Yoon | |
| 5,368,601 A | 11/1994 | Sauer et al. | |
| 5,374,275 A | 12/1994 | Bradley et al. | |
| 5,450,860 A | 9/1995 | O'Connor | 128/898 |
| 5,478,353 A * | 12/1995 | Yoon | 606/213 |
| 5,531,760 A * | 7/1996 | Alwafaie | 606/216 |
| 5,593,424 A | 1/1997 | Northrup, III | 606/232 |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | |
| 5,782,861 A * | 7/1998 | Cragg et al. | 606/216 |
| 5,800,495 A | 9/1998 | Machek et al. | 607/116 |
| 5,824,066 A | 10/1998 | Gross | 623/2 |
| 5,836,990 A | 11/1998 | Li | 607/28 |
| 5,865,791 A | 2/1999 | Whayne et al. | |
| 5,919,207 A | 7/1999 | Taheri | |
| 5,961,440 A | 10/1999 | Schweich, Jr. et al. | 600/16 |
| 5,964,782 A | 10/1999 | Lafontaine et al. | |
| 5,984,950 A * | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,104,944 A | 8/2000 | Martinelli | 600/424 |
| 6,113,610 A | 9/2000 | Poncet | |
| 6,132,438 A | 10/2000 | Fleischman et al. | |
| 6,203,554 B1 | 3/2001 | Roberts | |
| 6,210,432 B1 | 4/2001 | Solem et al. | 623/1.15 |
| 6,221,103 B1 | 4/2001 | Melvin | 623/3.1 |
| 6,221,104 B1 | 4/2001 | Buckberg et al. | 623/3.1 |
| 6,241,747 B1 * | 6/2001 | Ruff | 606/216 |
| 6,248,124 B1 | 6/2001 | Pedros et al. | |
| 6,258,258 B1 | 7/2001 | Sartori et al. | 208/263 |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,332,864 B1 | 12/2001 | Schweich, Jr. et al. | 600/16 |
| 6,346,105 B1 | 2/2002 | Tu et al. | 606/41 |
| 6,358,258 B1 * | 3/2002 | Arcia et al. | 606/139 |
| 6,360,749 B1 | 3/2002 | Jayaraman | 128/898 |
| 6,379,366 B1 * | 4/2002 | Fleischman et al. | 606/139 |
| 6,391,048 B1 | 5/2002 | Ginn et al. | |
| 6,391,054 B2 | 5/2002 | Carpentier et al. | 623/2.37 |
| 6,402,680 B2 | 6/2002 | Mortier et al. | 600/16 |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |
| 6,416,459 B1 | 7/2002 | Haindl | 600/37 |
| 6,436,052 B1 | 8/2002 | Nikolic et al. | 600/529 |
| 6,450,171 B1 | 9/2002 | Buckberg et al. | 128/898 |
| 6,475,223 B1 | 11/2002 | Werp et al. | 606/108 |
| 6,485,489 B2 | 11/2002 | Teirstein et al. | 606/41 |
| 6,506,210 B1 * | 1/2003 | Kanner | 606/213 |
| 6,537,198 B1 | 3/2003 | Vidlund et al. | 600/16 |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,589,208 B2 | 7/2003 | Ewers et al. | 604/104 |
| 6,626,930 B1 * | 9/2003 | Allen et al. | 606/213 |
| 6,632,238 B2 | 10/2003 | Ginn et al. | |
| 6,662,034 B2 | 12/2003 | Segner et al. | 600/373 |
| 6,676,685 B2 * | 1/2004 | Pedros et al. | 606/213 |
| 6,723,038 B1 | 4/2004 | Schroeder et al. | 600/16 |
| 6,726,704 B1 | 4/2004 | Loshakove et al. | |
| 6,726,716 B2 | 4/2004 | Marquez | 623/2.36 |
| 6,743,241 B2 * | 6/2004 | Kerr | 606/144 |
| 6,749,622 B2 | 6/2004 | McGuckin et al. | |
| 6,760,616 B2 | 7/2004 | Hoey et al. | 600/547 |
| 6,780,197 B2 | 8/2004 | Roe et al. | |
| 6,797,001 B2 | 9/2004 | Mathis et al. | 623/2.37 |
| 6,800,090 B2 | 10/2004 | Alferness et al. | 623/2.36 |
| 6,852,076 B2 | 2/2005 | Nikolic et al. | 600/37 |
| 6,855,143 B2 | 2/2005 | Davison et al. | 606/41 |
| 6,890,353 B2 | 5/2005 | Cohn et al. | 623/2.37 |
| 6,899,674 B2 | 5/2005 | Viebach et al. | 600/152 |
| 6,908,478 B2 | 6/2005 | Alferness et al. | 623/1.11 |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,028 B2 | 1/2006 | Lashinski et al. | 623/2.37 |
| 6,994,093 B2 | 2/2006 | Murphy et al. | 128/898 |
| 6,997,951 B2 | 2/2006 | Solem et al. | 623/2.37 |
| 7,025,776 B1 | 4/2006 | Houser et al. | |
| 7,050,848 B2 | 5/2006 | Hoey et al. | 600/547 |
| 7,052,487 B2 | 5/2006 | Cohn et al. | 604/509 |
| 7,144,363 B2 | 12/2006 | Pai et al. | 600/16 |
| 7,177,677 B2 | 2/2007 | Kaula et al. | 600/546 |
| 7,186,210 B2 | 3/2007 | Feld et al. | 600/16 |
| 7,189,202 B2 | 3/2007 | Lau et al. | 600/37 |
| 7,279,007 B2 | 10/2007 | Nikolic et al. | 623/11.11 |
| 7,300,435 B2 | 11/2007 | Wham et al. | 606/34 |
| 7,303,526 B2 | 12/2007 | Sharkey et al. | 600/37 |
| 7,507,252 B2 | 3/2009 | Lashinski et al. | 623/2.37 |
| 2001/0003158 A1 | 6/2001 | Kensey et al. | |
| 2001/0005787 A1 * | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2001/0044568 A1 | 11/2001 | Langberg et al. | 600/37 |
| 2002/0016628 A1 | 2/2002 | Langberg et al. | 623/2.36 |
| 2002/0026092 A1 | 2/2002 | Buckberg et al. | 600/37 |
| 2002/0055775 A1 | 5/2002 | Carpentier et al. | 623/2.17 |
| 2002/0082621 A1 * | 6/2002 | Schurr et al. | 606/151 |
| 2002/0087173 A1 | 7/2002 | Alferness et al. | 606/151 |
| 2002/0115944 A1 | 8/2002 | Mendes et al. | 600/594 |
| 2002/0161394 A1 | 10/2002 | Macoviak et al. | 606/200 |
| 2002/0169359 A1 | 11/2002 | McCarthy et al. | 600/16 |
| 2002/0169360 A1 | 11/2002 | Taylor et al. | 600/37 |
| 2002/0169504 A1 | 11/2002 | Alferness et al. | 623/2.36 |
| 2002/0183836 A1 | 12/2002 | Liddicoat et al. | 623/2.11 |
| 2002/0183841 A1 | 12/2002 | Cohn et al. | 623/2.36 |
| 2002/0188170 A1 | 12/2002 | Santamore et al. | 600/37 |
| 2002/0198603 A1 | 12/2002 | Buckberg et al. | 623/23.71 |
| 2003/0045896 A1 | 3/2003 | Murphy et al. | 606/191 |
| 2003/0050682 A1 | 3/2003 | Sharkey et al. | 607/126 |
| 2003/0050685 A1 | 3/2003 | Nikolic et al. | 623/1.11 |
| 2003/0069570 A1 | 4/2003 | Witzel et al. | 606/28 |
| 2003/0069636 A1 | 4/2003 | Solem et al. | 623/2.37 |
| 2003/0078465 A1 | 4/2003 | Pai et al. | 600/16 |
| 2003/0078671 A1 | 4/2003 | Lesniak et al. | 623/23.64 |
| 2003/0105384 A1 | 6/2003 | Sharkey et al. | 600/16 |
| 2003/0105520 A1 | 6/2003 | Alferness et al. | 623/2.36 |
| 2003/0109770 A1 | 6/2003 | Sharkey et al. | 600/16 |
| 2003/0149333 A1 | 8/2003 | Alferness | 600/16 |
| 2003/0163191 A1 | 8/2003 | Nikolic et al. | 623/1.11 |
| 2003/0220667 A1 | 11/2003 | van der Burg et al. | 606/200 |
| 2003/0229395 A1 | 12/2003 | Cox | 623/2.36 |
| 2004/0002626 A1 | 1/2004 | Feld et al. | 600/37 |
| 2004/0054279 A1 | 3/2004 | Hanley | 600/424 |
| 2004/0133273 A1 | 7/2004 | Cox | 623/2.11 |
| 2004/0138529 A1 * | 7/2004 | Wiltshire et al. | 600/144 |
| 2004/0138744 A1 | 7/2004 | Lashinski et al. | 623/2.36 |
| 2004/0153146 A1 | 8/2004 | Lashinski et al. | 623/2.36 |
| 2004/0158321 A1 | 8/2004 | Reuter et al. | 623/2.36 |
| 2004/0186566 A1 | 9/2004 | Hindrichs et al. | 623/2.37 |
| 2004/0215232 A1 | 10/2004 | Belhe et al. | |
| 2004/0243170 A1 | 12/2004 | Suresh et al. | 606/198 |
| 2004/0249408 A1 | 12/2004 | Murphy et al. | 606/198 |
| 2004/0249453 A1 | 12/2004 | Cartledge et al. | 623/2.37 |
| 2004/0267358 A1 | 12/2004 | Reitan | 623/2.37 |

| | | | |
|---|---|---|---|
| 2005/0004668 A1 | 1/2005 | Aklog et al. ............... 623/2.36 |
| 2005/0015109 A1 | 1/2005 | Lichtenstein ............... 606/200 |
| 2005/0054938 A1 | 3/2005 | Wehman et al. ............ 600/483 |
| 2005/0055089 A1 | 3/2005 | Macoviak et al. .......... 623/2.37 |
| 2005/0060030 A1 | 3/2005 | Lashinski et al. .......... 623/2.37 |
| 2005/0064665 A1 | 3/2005 | Han ........................... 438/286 |
| 2005/0080402 A1 | 4/2005 | Santamore et al. ............. 606/1 |
| 2005/0096047 A1 | 5/2005 | Haberman et al. ....... 455/432.3 |
| 2005/0107723 A1 | 5/2005 | Wehman et al. ............. 600/595 |
| 2005/0107871 A1* | 5/2005 | Realyvasquez et al. .... 623/2.11 |
| 2005/0125030 A1 | 6/2005 | Forsberg |
| 2005/0137700 A1 | 6/2005 | Spence et al. .............. 623/2.36 |
| 2005/0149014 A1 | 7/2005 | Hauck et al. .................. 606/41 |
| 2005/0149114 A1 | 7/2005 | Cartledge et al. ........... 606/213 |
| 2005/0154252 A1 | 7/2005 | Sharkey et al. ................ 600/37 |
| 2005/0182365 A1 | 8/2005 | Hennemann et al. ........ 604/113 |
| 2005/0187620 A1 | 8/2005 | Pai et al. .................... 623/2.37 |
| 2005/0197692 A1 | 9/2005 | Pai et al. ...................... 623/2.1 |
| 2005/0197693 A1 | 9/2005 | Pai et al. ...................... 623/2.1 |
| 2005/0197694 A1 | 9/2005 | Pai et al. ...................... 623/2.1 |
| 2005/0197716 A1 | 9/2005 | Sharkey et al. ........... 623/23.67 |
| 2005/0209636 A1 | 9/2005 | Widomski et al. |
| 2005/0216052 A1 | 9/2005 | Mazzocchi et al. .......... 606/200 |
| 2005/0216054 A1 | 9/2005 | Widomski et al. |
| 2005/0240249 A1 | 10/2005 | Tu et al. ....................... 607/96 |
| 2005/0251116 A1 | 11/2005 | Steinke et al. .................. 606/8 |
| 2005/0267574 A1 | 12/2005 | Cohn et al. ................ 623/2.36 |
| 2006/0014998 A1 | 1/2006 | Sharkey et al. ................ 600/16 |
| 2006/0015002 A1 | 1/2006 | Moaddeb et al. .............. 600/37 |
| 2006/0015003 A1 | 1/2006 | Moaddes et al. .............. 600/37 |
| 2006/0015038 A1 | 1/2006 | Weymarn-Scharli ........ 600/585 |
| 2006/0025800 A1 | 2/2006 | Suresh ........................ 606/198 |
| 2006/0030881 A1 | 2/2006 | Sharkey et al. .............. 606/213 |
| 2006/0135968 A1 | 6/2006 | Schaller ...................... 606/144 |
| 2006/0135970 A1 | 6/2006 | Schaller ...................... 606/152 |
| 2006/0184242 A1 | 8/2006 | Lichtenstein ............... 623/2.37 |
| 2006/0199995 A1 | 9/2006 | Vijay ........................... 600/37 |
| 2006/0229491 A1 | 10/2006 | Sharkey et al. ................ 600/37 |
| 2006/0235286 A1 | 10/2006 | Stone et al. ................. 600/381 |
| 2006/0241334 A1 | 10/2006 | Dubi et al. .................... 600/16 |
| 2006/0264980 A1 | 11/2006 | Khairkhahan et al. ....... 606/153 |
| 2006/0276683 A1 | 12/2006 | Feld et al. ..................... 600/16 |
| 2006/0281965 A1 | 12/2006 | Khairkhahan et al. ......... 600/37 |
| 2006/0293698 A1 | 12/2006 | Douk .......................... 606/142 |
| 2007/0016068 A1 | 1/2007 | Grunwald et al. ........... 600/468 |
| 2007/0118215 A1 | 5/2007 | Moaddeb ................... 623/2.37 |
| 2007/0161846 A1 | 7/2007 | Nikolic et al. ................. 600/16 |
| 2007/0198058 A1 | 8/2007 | Gelbart et al. .............. 606/213 |
| 2007/0213578 A1 | 9/2007 | Khairkhahan et al. ......... 600/16 |
| 2007/0213815 A1 | 9/2007 | Khairkhahan et al. ........ 623/3.1 |
| 2007/0219460 A1* | 9/2007 | Goldenberg ................ 600/566 |
| 2007/0250160 A1 | 10/2007 | Rafiee ......................... 623/2.11 |
| 2007/0270688 A1 | 11/2007 | Gelbart et al. .............. 600/427 |
| 2008/0004643 A1 | 1/2008 | To et al. ...................... 606/159 |
| 2008/0004697 A1 | 1/2008 | Lichtenstein et al. ....... 623/2.11 |
| 2008/0045778 A1 | 2/2008 | Lichtenstein et al. .......... 600/16 |
| 2008/0071298 A1 | 3/2008 | Khairkhahan et al. ....... 606/151 |
| 2008/0086164 A1 | 4/2008 | Rowe ......................... 606/191 |

FOREIGN PATENT DOCUMENTS

| | | |
|---|---|---|
| WO | 01/78625 | 10/2001 |
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/070330 | 8/2005 |
| WO | 2005/102181 | 11/2005 |
| WO | 2006/017809 | 2/2006 |
| WO | 2006/135747 | 12/2006 |
| WO | 2006/135749 | 12/2006 |
| WO | 2007/021647 | 2/2007 |
| WO | 2007/115390 | 10/2007 |

OTHER PUBLICATIONS

U.S. Appl. No. 10/690,131, filed Oct. 20, 2003, Lichtenstein.
U.S. Appl. No. 11/400,260, filed Apr. 10, 2006, Lichtenstein.
U.S. Appl. No. 11/436,584, filed May 19, 2006, Gelbart et al.
U.S. Appl. No. 11/475,978, filed Jun. 28, 2006, Lichtenstein et al.
U.S. Appl. No. 11/497,309, filed Aug. 2, 2006, Lichtenstein et al.
U.S. Appl. No. 12/120,195, filed May 13, 2008, Dahlgren et al.
Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.
Konings et al., "Development of an Intravascular Impedance Catheter for Detection of Fatty Lesions in Arteries," *IEEE Transactions on Medical Imaging*, 16(4):439-446, 1997.
Mack, "New Techniques for Percutaneous Repair of the Mitral Valve," *Heart Failure Review*, 11:259-268, 2006.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering*, 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching ('SLAC') Reduces Mitral Annular Size Without Perturbing Normal Annular Dynamics," *Journal of Heart Valve Disease* 11(1):2-10, 2002.
Timek et al., "Septal-Lateral Annular Cinching Abolishes Acute Ischemic Mitral Regurgitation," *Journal of Thoracic and Cardiovascular Surgery*, 123(5):881-888, 2002.
Valvano et al., "Thermal Conductivity and Diffusivity of Biomaterials Measured with Self-Heated Thermistors," *International Journal of Thermodynamics*, 6(3):301-311, 1985.
Athanasuleas et al., "Surgical Anterior Ventricular Restoration for Ischemic Cardiomyopathy," *Operative Techniques in Thoracic and Cardiovascular Surgery* 7(2):6675, May 2002.
Cooley, "Ventricular Aneurysms and Akinesis," *Cleveland Clinic Quarterly* 45(1):130-132, 1978.
David et al., "Postinfarction Ventricular Septal Rupture: Repair by Endocardial Patch with Infarct Exclusion," *Journal of Thoracic and Card Surgery* 110(5):1315-1322, 1995.
Dor et al., "Left Ventricular Aneurysm: A New Surgical Approach," *Thoracic Cardiovascular Surgery* 37:11-19, 1989.
Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.
Dor, "Left Ventricular Aneurysms: The Endoventricular Circular Patch Plasty," *Seminars in Thoracic and Cardiovascular Surgery* 9(2):123-130, Apr. 1997.
Jatene, "Left Ventricular Aneurysmectomy," *Journal of Thoracic and Cardiovascular Surgery* 89(3):321-331, 1985.
Menicanti et al., "The Dor Procedure: What has Changed After Fifteen Years of Clinical Practice?" *Journal of Thoracic and Cardiovascular Surgery* 124(5):886-890, Nov. 2002.
Rivera et al., "Ventricular Aneurysms and Akinesis," *Cleveland Clinic Quarterly* 45(1):133-135, 1978.
Torrent-Guasp et al., "Spatial Orientation of the Ventricular Muscle Band and Approach to Partial Ventriculotomy in Heart Failure," *Pathogenesis and Treatment*, Ch. 36, pp. 685-693.

* cited by examiner

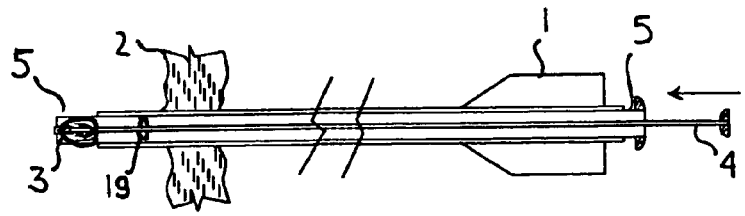
FIG. 2-a
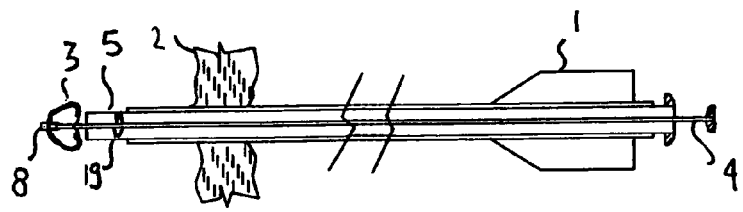
FIG. 2-b
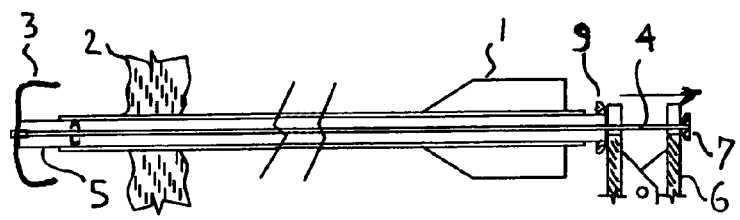
FIG. 2-c
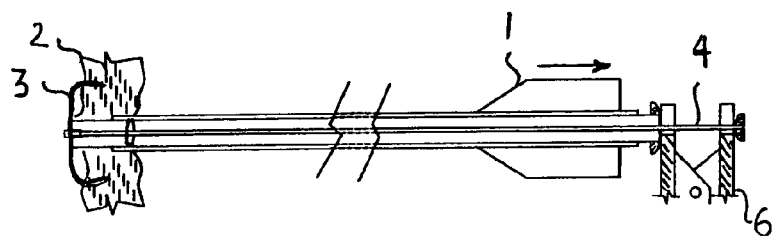
FIG. 2-d
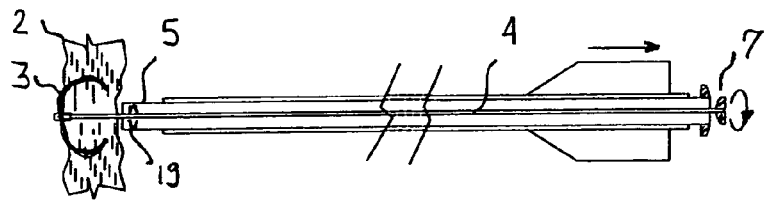
FIG. 2-e
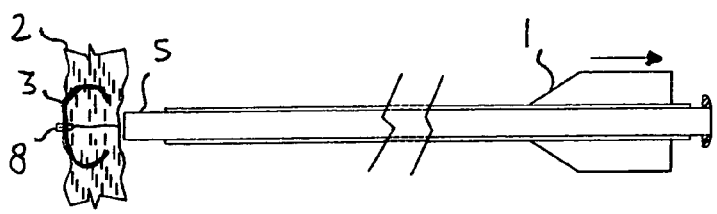
FIG. 2-f

FIG.6-a
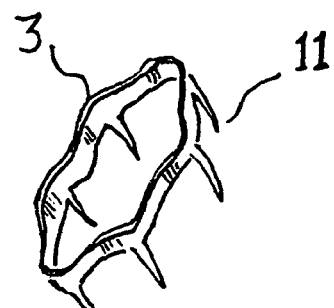
FIG.6-b
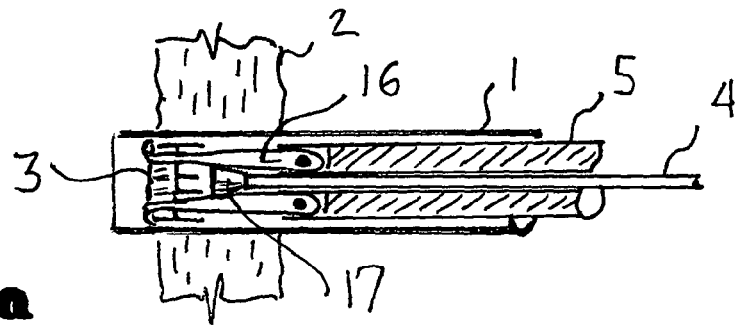
FIG.7-a
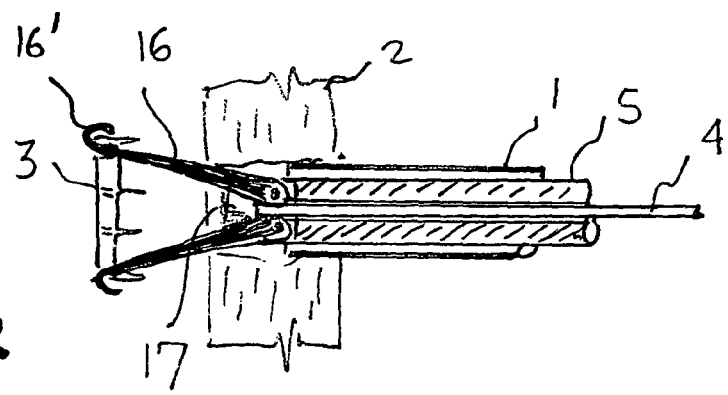
FIG.7-b

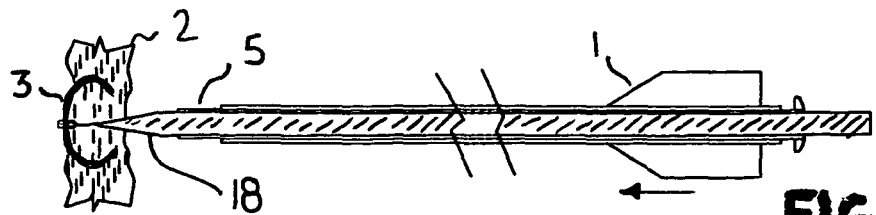
FIG.8-a
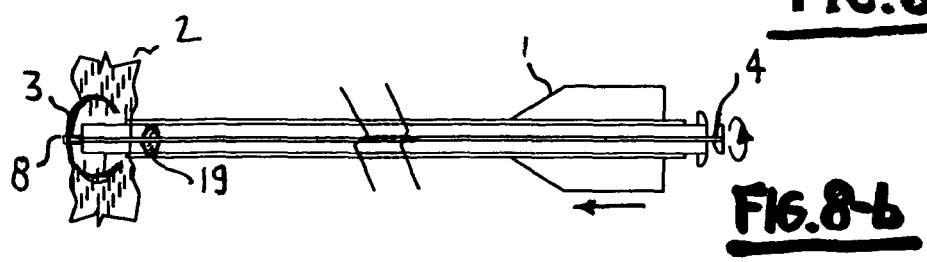
FIG.8-b
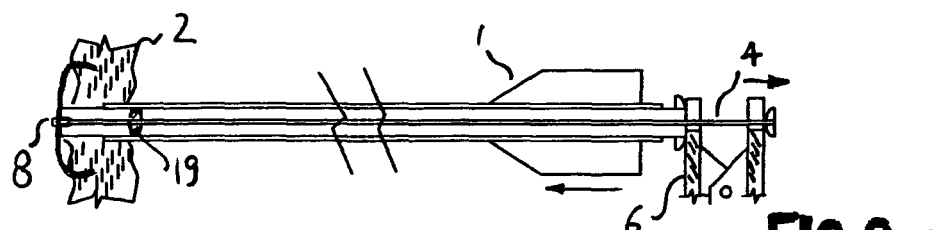
FIG.8-c
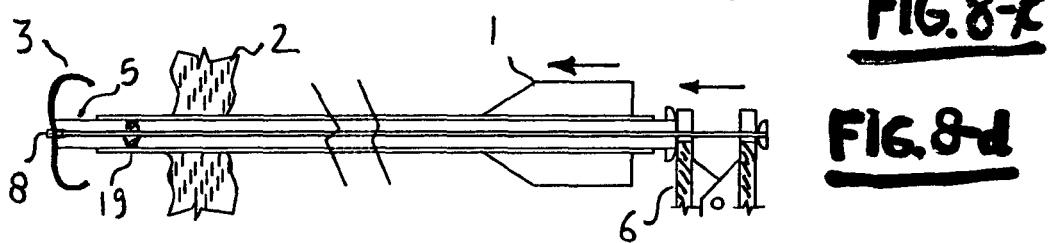
FIG.8-d
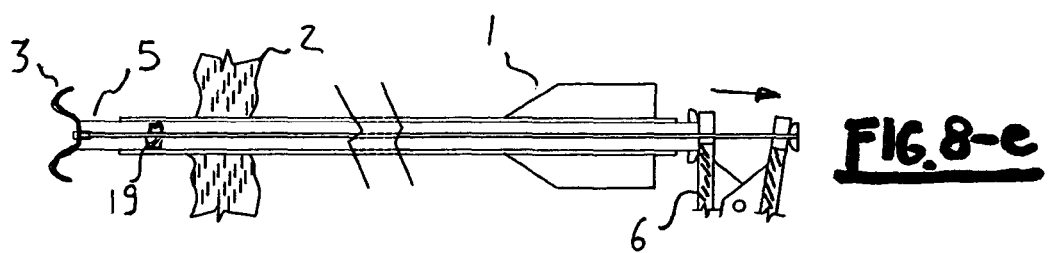
FIG.8-e
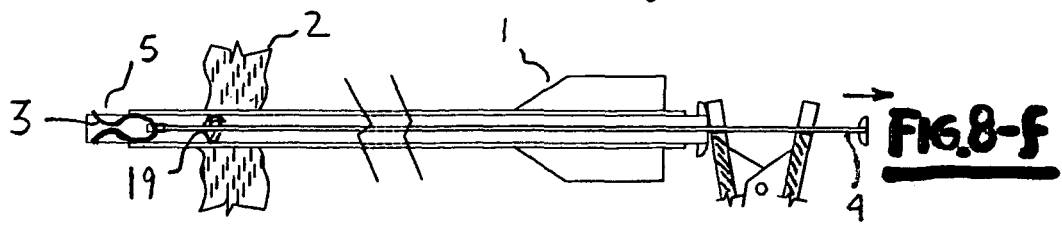
FIG.8-f

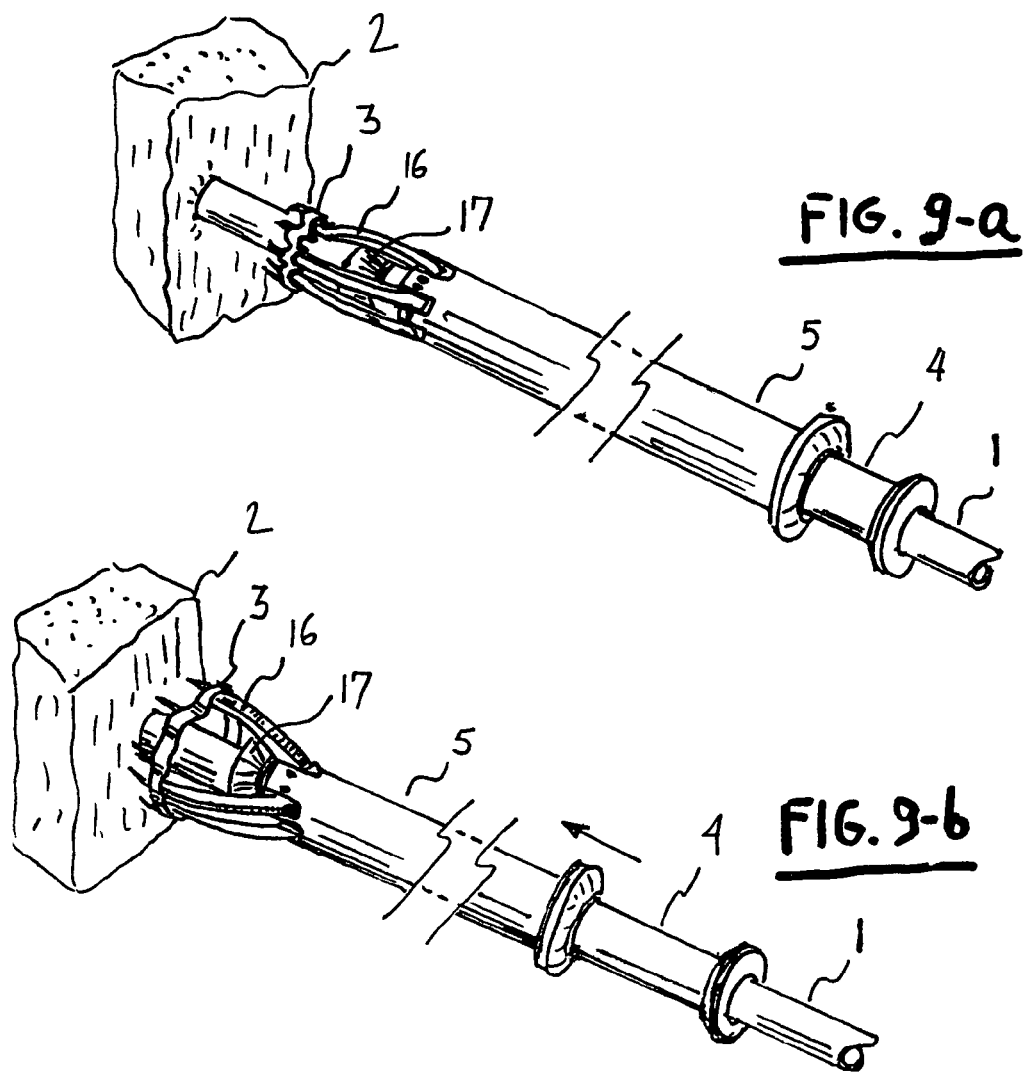
FIG. 9-a
FIG. 9-b

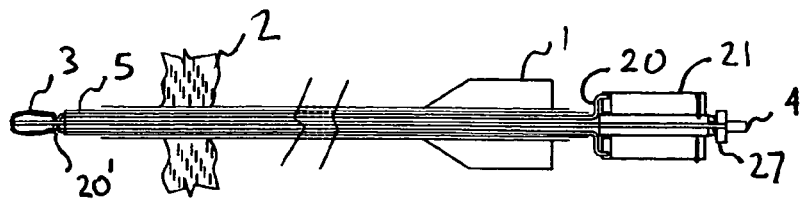
FIG.13-a
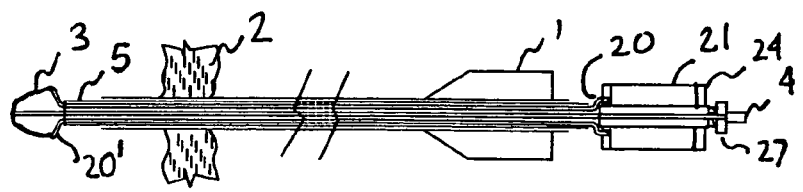
FIG.13-b
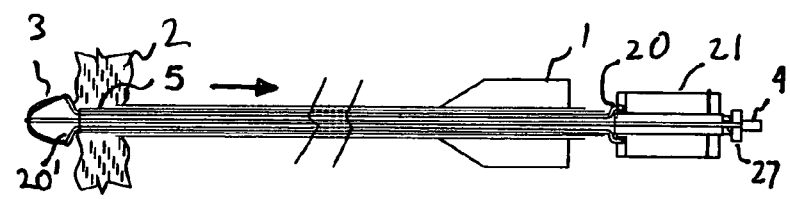
FIG.13-c
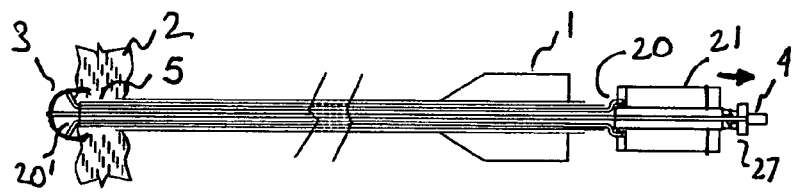
FIG.13-d
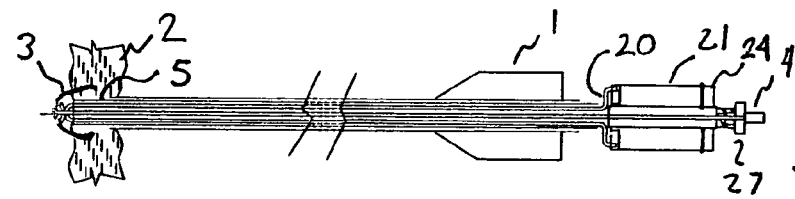
FIG.13-e
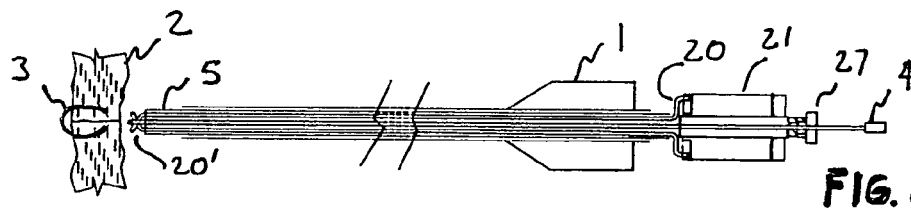
FIG.13-f

METHOD AND DEVICE FOR CLOSING HOLES IN TISSUE

This application is a CIP of Ser. No. 11/357,011 filed on Feb. 21, 2006 and ABN.

FIELD OF THE INVENTION

The present invention relates to surgery and in particular to closing holes in tissue during minimally invasive surgery. The invention is particularly useful for closing holes left by catheters during percutaneous surgical procedures such as minimally invasive cardiac surgery and other surgeries requiring access to body lumens.

BACKGROUND OF THE INVENTION

More and more surgical procedures are performed percutaneously by the use of catheter-delivered devices. The main advantages are fast patient recovery and lower costs to the medical system. Some tissues, such as muscular tissue or arterial walls, do not seal well and are sometimes subject to blood pressure; therefore they require an immediate hemostatic seal after the surgery. Prior art solutions mainly rely on some form of a plug, such as an expanding foam plug, expanding metal plug or a barbed plug to seal the hole. The main disadvantage of plugs is that in order to form a good seal they are forcing the hole to become larger, rather than the more natural way which is to shrink the hole in order to promote healing. A prior art device operating by shrinking the hole is the Star Closure device sold by Abbott Vascular (www.abbottvasculardevices.com) however this device is only suitable to thin walled body lumens as it relies on folding the tissue. When sealing larger holes in thicker tissue the gripping points for pulling the tissue inwards have to be spread over an area significantly larger than the hole size, similar to what is done in traditional suturing. Attaching the closure device too close to the hole does not allow sufficient forces to be applied, therefore creating a marginal closure.

Another major shortcoming of the Star Closure and other devices is that the operation is not reversible. It is sometimes required to remove the closure, as in the case of bleeding or an additional procedure.

It is therefore desired to provide a hole closure method that provides an immediate liquid and gas tight closure and it can be delivered by a catheter to the inside wall of a body lumen.

It is also desired to provide a closure method suitable for a large range of tissue thicknesses and hole sizes.

It is also desired to be able to test, and if required to remove, the closure.

It further would be desired for the closing device to have permanent elastic properties to accommodate any movement or future changes in the tissue. Furthermore, the gripping area of the closure device has to be significantly larger than the original hole.

SUMMARY OF THE INVENTION

In view of the foregoing, the invention provides a method and device for closing holes in body lumens, and in particular in the heart and blood vessels, achieving an immediate hemostatic seal. The device can be applied via a wide range of catheters sizes to close a wide range of round and elongated holes with performance and reliability of traditional sutures but without requiring access to the tissue, except via the catheter. Furthermore, the device can be removed via the same catheter, and by using the same tools used to install it and can be re-used immediately if so desired. The device has a high degree of elastic compliance allowing a wide accommodation range to changes in the tissue. These and other objects of the present invention are achieved by providing a flexible clip that is temporarily attaches to an insertion tool. The clip has three different positions: a storage position, in which it is folded inside a delivery tube; an expanded position, in which it opens up to reach an area significantly larger than the hole, and a closed position in which elastic forces try to close the clip, pulling the tissue with it to close the hole. The clip has multiple sharp barbs for gripping the tissue and a stem for attaching to the insertion tool, as well as for re-attaching in case removal is required.

Methods for implanting and removal of the device are also provided.

The invention will become apparent by studying the drawings and the detailed description.

BRIEF DESCRIPTION OF THE DRAWING

FIG. 2-$a$ to FIG. 2-$f$ are sectional views showing the steps in installing the device using the installation tool.

FIG. 6-$a$ is a perspective view of an alternate embodiment in the relaxed state.

FIG. 6-$b$ is a perspective view of the same alternate embodiment in the expanded state.

FIG. 7-$a$ is a sectional view of the tool used to install the device embodiment of FIG. 6-$a$ in the relaxed state.

FIG. 7-$b$ is a sectional view of the tool used to install the device embodiment of FIG. 6-$a$ in the expanded state.

FIG. 8-$a$ to FIG. 8-$f$ are sectional views showing the steps in removing the device, FIG. 9-$a$ and FIG. 9-$b$ are perspective views of a device installed on the outside of a catheter.

FIG. 12-$b$ is a perspective view of the preferred embodiment in the retracted position.

FIG. 13-$a$ to FIG. 13-$f$ are sectional view of the preferred embodiment showing the steps in installing the device.

DETAILED DESCRIPTION OF THE INVENTION

Figure 1:
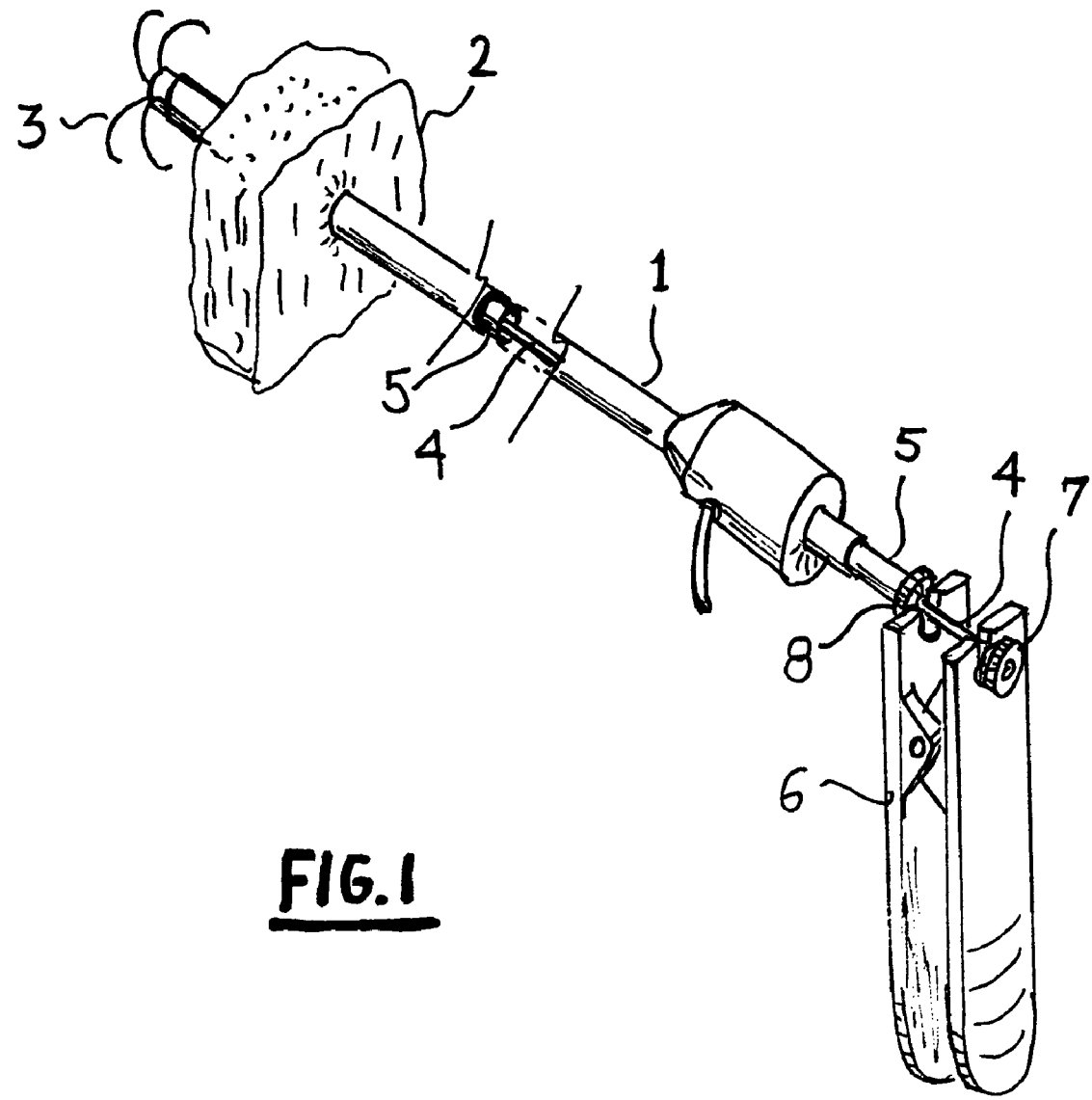
FIG. 1 is a perspective view of the invention and the installation tool.

Referring to FIG. 1, a hole closure clip 3 is inserted into a body lumen such a cavity in the heart via catheter 1. Catheter 1 has a seal allowing insertion and removal of tools without much blood loss. This is well known in the art of minimally invasive surgery. When the surgical procedure is completed and hole needs to be closed, tube 5 carrying clip 3 mounted on rod 4 is inserted via catheter 1 through the tissue 2. Both rod 4 and tube 5 have flanges 7 and 8 allowing a pulling tool 6 to exert a significant pulling force on rod 4 relative to tube 5. Pulling tool 6 may be made of plastic or metal, plastic being preferred if tool is to be disposable. Rod 4 and tube 5 are preferable made of stainless steel and closure device 3 is made of Nitinol, a highly flexible Nickel.Ti~anium alloy well known in the art of medical devices. Tool 6 is similar in construction t the well known clothe-pin. Since the elastic range of Nitinol is about ten times larger than steel, the clip 3 can be made to fold into a small diameter tube and expand to grip the tissue over an area significantly larger than the area of the hole, in order to establish reliable closure. When clip 3 is released it tries to return to its natural (relaxed) shape, which covers a significantly smaller area, pulling the tissue with it and forming an instant hemostatic seal. These steps are shown in FIG. 2-*a* to FIG. 2-*f*.

Figure 3:
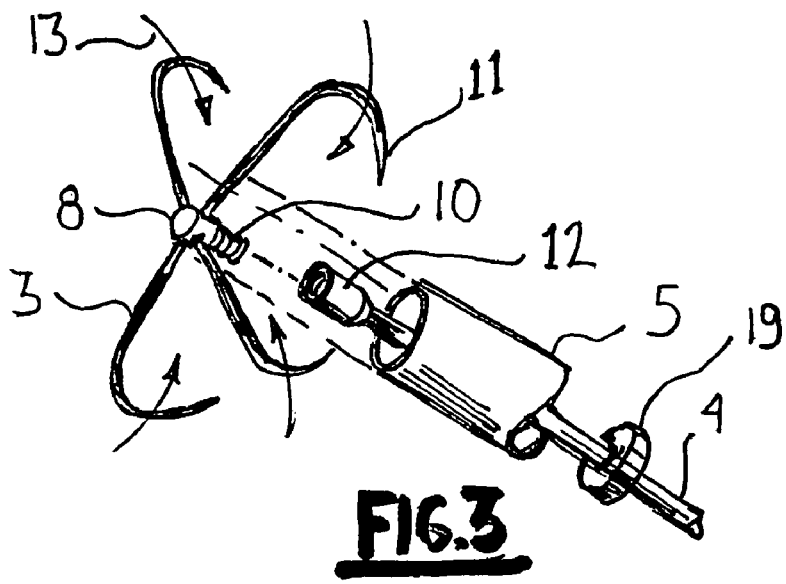
FIG. 3 is a perspective "exploded" view of the device.

In FIG. 2-*a* the tube 5 containing the folded clip 3 mounted on rod 4 is inserted via catheter 1 through the wall of the tissue 2. Rod 4 is pushed forward by finger pressure till it is felt that clip 3 is released from tube 5 (or moved till it reaches a pre-determined distance), as shown in FIG. 2-*b*. At this pint it is pulled back and pulling tool 6 is installed by sliding it on rod 4. Pulling tool 6 can be permanently mounted on rod 4 or slide in and out via two slots as shown in Figi. The slots rest against flanges 7 and 8. Flange 7 is rigidly connected to rod 4 while flange 8 is rigidly connected to tube 5. Using pulling tool 6, rod 4 is pulled out a pre-determined amount which forces clip 3 to open as shown in FIG. 2-*c*, as it rests against end of tube 5. At this point the whole assembly, including catheter 1, is pulled back to engage the sharp barbs of tool 3 in tissue 2. This is shown in FIG. 2-*d*. An enlarged view of clip 3 is shown in FIG. 3. In FIG. 3, clip 3 comprises of multiple sharp barbs 11 held by a threaded stem 8. Clip 3, including barbs 11 are made of Nitinol wire typically 0.3-0.8 mm in diameter, Stem 8 can be made of type 316 stainless steel and held to wires by crimping. It contains a threaded portion 10 for attaching to rod 4. The end of rod 4 has a mating thread 12. When clip 3 rests on edge of tube 5 it can be opened widely by pulling rod 4 and barbs 11 can reach over an area having a diameter from 1.5 to over 3 times the diameter of the hole. This is important to achieve proper hemostatic closure. When rod 4 is detached from clip 3, the natural elasticity pulls barb 11 in the direction shown by arrows 13 and the tissue is pulled with them. Centering ferrule 19 on rod 4 keeps the location of clip 3 centered to tube 5, therefore centered to hole in tissue. Returning now to FIG. 2-*e*, pulling tool 6 is released and removed allowing clip 3 to compress the tissue. Rod 4 is removed by turning flange 7 to unthread rod. After rod is removed the closure can be tested for leaks by leaving tube 5 in place. When used in the heart, any imperfection in closure will cause blood to come out of tube 5. In such a case the clip 3 can be removed and re-installed as shown later on in this disclosure. One verified, both tube 5 and catheter 1 are removed.

Figure 4:
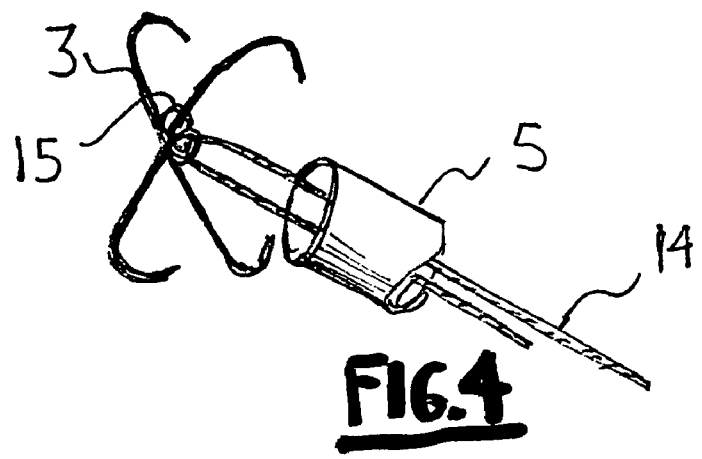
FIG. 4 is a perspective "exploded" view of an alternate embodiment.

FIG. 4 shows an alternate design for clip 3. The main differences are that the Nitinol wire is bent into a loop 15 to add elasticity and a string 14 is used as a method of holding clip 3 to tube 5. The string can be removed by releasing one end.

Figure 5:
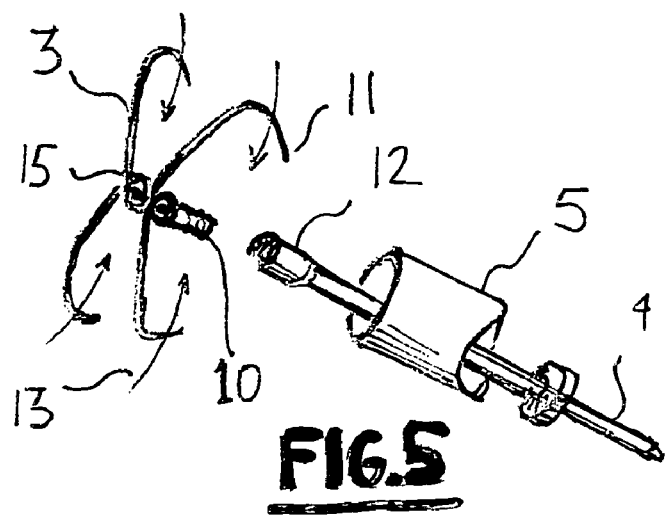
FIG. 5 is an "exploded" view of another alternate embodiment.

FIG. 5 shows another alternate design, preferred when hole is an elongated cut rather than a round hole. Clip 3 is bent to have barbs 11 move in parallel rather than radially, as shown by arrows 13. Clip 3 is placed with the direction of motion 11 perpendicular to long dimension of hole in tissue. Loops 15 are used to add elasticity, as in FIG. 4.

FIG. 6 shows yet another alternate design. The clip 3 can be fabricated from Nitinol sheet, tubing or wire. The preferred way would be laser-cut tubing. FIG. 6-*a* shows the clip in the relaxed state, FIG. 6-*b* shows it in the expanded state. This design is suitable when a large number of barbs 111 are desired or for thin-walled lumens.

The tool used to expand the clip is shown in FIG. 7-*a* (relaxed state) and FIG. 7-*b* (expanded state). Rod 4 is equipped with a tapered end 17 used to expand four pivoting arms 16. The sequence of operations is identical to the sequence shown in FIG. 2-*a* to FIG. 2-*f*.

It is desirable to be able to reverse the clip installation and, if needed, remove the clip completely via the same catheter used to install it. The current inventions~, in all its forms, allows this to be done. Referring now to FIG. 8-*a* to FIG. 8-*f*: the sequence of partial and full removal is shown.

In FIG. 8-*a* a dilator 18 is used to expand the opening in the tissue 2 as well as the surrounding tissue, in order to feed tube 5 back into its original position. In FIG. 8-*b* Rod 4 is inserted in tube 5 and is attached to clip 3 by threading it onto stem 8 of clip 3. Centering ferrule 19 keeps rod 4 aligned with stem 8. Tool 6 in mounted on rod 4 and used to expand slip 3 as shown in FIG. 8-*c*. Once expanded, the whole assembly of catheter 1 and tube 5 is pushed forward to remove clip 3 from tissue 2, as shown in FIG. 8-*d*. At this point clip 3 can be re-installed following the steps in FIG. 2-*c* to FIG. 2-*f* or removed completely by pulling clip into tube 5 as shown in FIG. 8-*e* and FIG. 8-*f*. Once clip 3 is fully inside tube 5, it can be easily pulled out by hand using rod 4. If desired, clip 3 can be re-used immediately by pushing it back into tube 5 to assume the position shown in FIG. 2-*a*. When the clip style shown in FIG. 4 is used, the retrieval tool is equipped with a small hook to engage with loop 15.

The large elastic range of Nitinol allows full removal without permanently deforming clip 3. Because of this large elasticity, clip 3 can not be manufactured by cold forming. It has to be held in the relaxed position (shown in FIG. 2-*b*) and heated to about 510 degrees C. for a few minutes. The exact heat treatment details given by the manufacturer of the Nitinol wire have to be carefully followed.

While the invention will work for any dimension of catheter, the preferred range is for catheters with internal diameters of 4 mm to 15 mm. The Nitinol wire diameter is about 0.4 mm for the 4 mm catheter and about 1 mm for the 15 mm catheter. The thread 10 on stem 8 is from M1 for the 4 mm catheter to M4 on the 15 mm catheter, M2 being a typical value. Tube 5 is made from standard stainless hypodermic tubing. All materials to construct the invention are available from Small Parts Inc (www.smallparts.com). While the detailed description showed a specific embodiment of a clip with four barbs, it is obvious that the inventions covers many other configurations of barbs, made from many materials including materials used to make absorbable sutures and other non-metallic clips. It is also obvious that the invention can be configured to be used on the outside rather than the inside wall of the body lumen by sliding a clip shown in FIG. 6-*b* on the outside of tube 5 and expanding it with the method shown in FIG. 7-*b*.

This is shown in FIG. 9-*a* (closed position) and 9-*b* (open position). Tubes 4 and 5 slide over catheter 1 (but can be inside a larger catheter, not shown). Catheter 1 penetrates the wall of tissue 2 but tube 5 only reaches to the outside of tissue 2. Clip 3 is expanded by arms 16 actuated by taper 17 connected to tube 4. Many alternate expansion mechanisms are well known. After clip 3 is embedded in tissue 2, arms 16 are retracted and tubes 4 and 5 are withdrawn.

Figure 10:
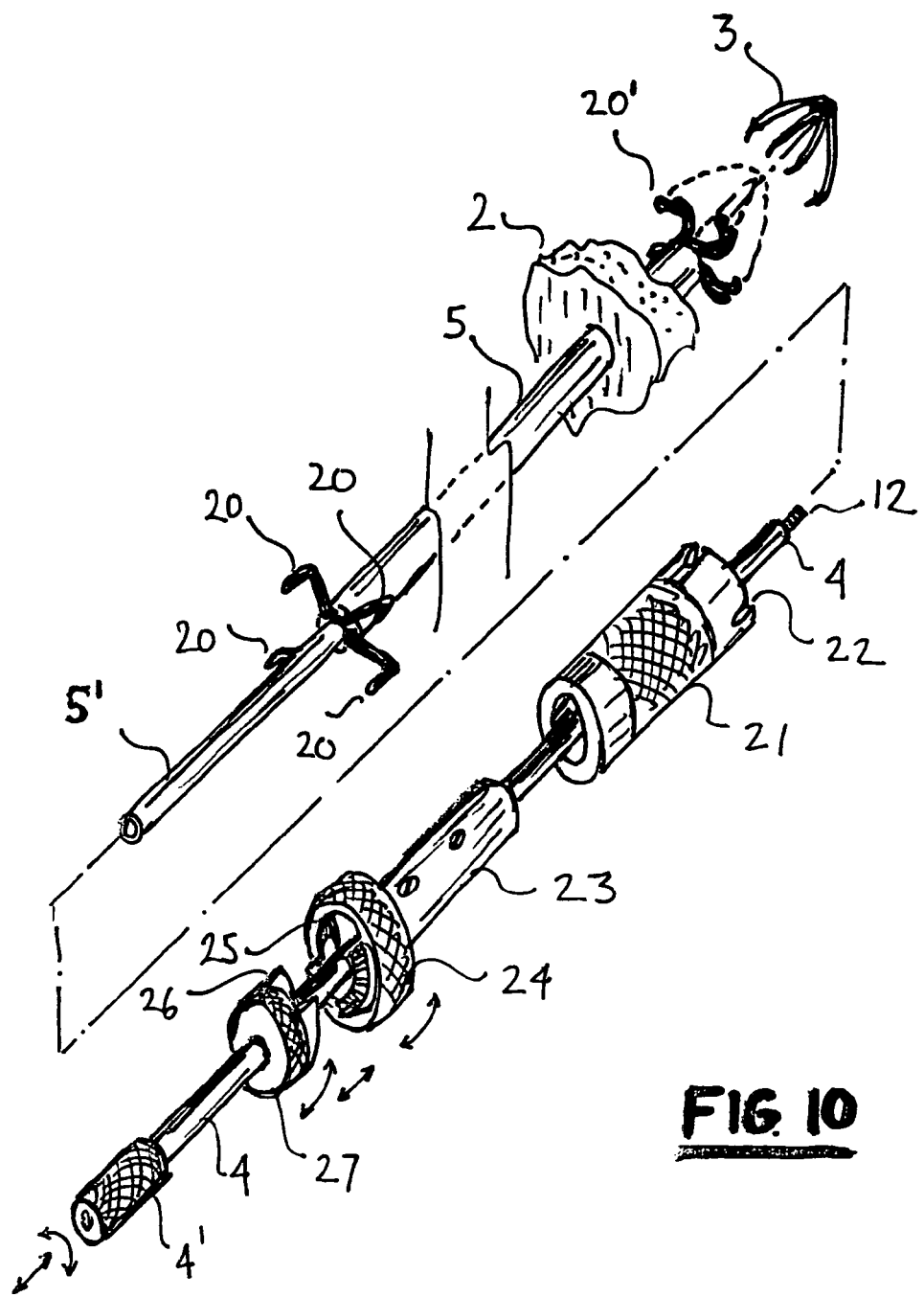
FIG. 10 is an "exploded" view of the preferred embodiment.

The preferred embodiment is shown in FIG. 10 as an "exploded" view. This embodiment used similar clips as the previous embodiments and a slightly more complex installation tool. The main additional advantages of this embodiment are:

ability to locate the tool within a lumen without use of monitoring such as x-ray or ultrasound.

ability to move the tool within the lumen without damage to the surrounding tissue.

To achieve these and further objectives, the sharp barbs of the clip are covered till ready to be embedded, and the tool provides a positive stop to locate the inside wall of the tissue. In FIG. 10 clip 3 is threaded onto the end of rod 4 via thread 12. A tube 5, made from extruded plastic or metal, has five holes running through it. Four of the holes are used for actuators 20 ending in arms 20'. The fifth hole is for rod 4. Actuators 20 can rotate inside tube 5 approximately 180 degrees, opening and closing clip 3. Actuators 20 engage in corresponding slots 22 in sleeve 21, which is free to rotate over shaft 23 which is clamped to extension 5' of tube 5. Rod 4 terminates in a section 4' resting on disc 27. By rotating disc 27 relative to shaft 23, disc 27 is moved axially away from shaft 23. This is achieved via inclined planes 25 and 26 but can be achieved by any one of the well known mechanisms converting rotary to linear motion such as threads, cams etc. When disc 27 is moved axially, it pulls rod 4 with it, causing clip 3 to slide over arms 20' and expand further. In operation, the tool is held by sleeve 21 and ring 24 is rotated to cause tune 5 to rotate. Since ends of actuators 20 are in slots 22, rotating tube 5 will cause actuators 20 to rotate and expand clip 3. After tool is in position, disc 27 is rotated to pull clip over arms 20' and embed barbs in tissue, followed by releasing the tool by turning end 4' of rod 4 to release tool from clip.

Figure 11:
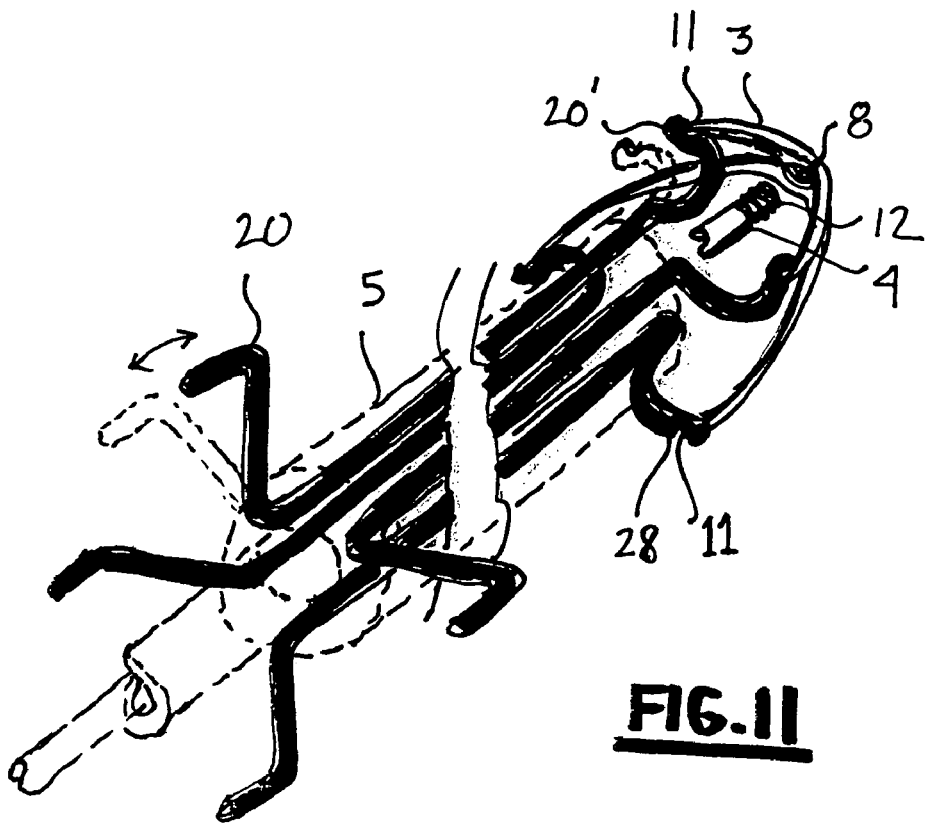
FIG. 11 is a "phantom" view of the actuation mechanism.

FIG. 11 is an enlarged view of both ends of actuators 20. At the end of each arm 20' there is a recess 28 into which barbed tip 11 of clip 3 fits. This provides a smooth outside surface till the barbs are exposed, and allows the tool to be moved inside a body lumen without damage. For example, when the device is used inside the heart, it is imperative to avoid snagging or damaging any one of the many cords attached to the valves. Clip 3 is attached to rod 4 via a thread 8 at center of clip.

Figure 12:
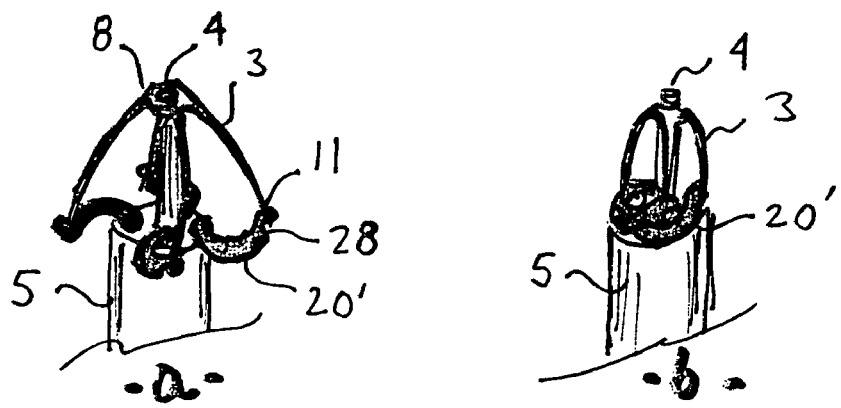
FIG. 12-$a$ is a perspective view of the preferred embodiment in the fully open position.

FIG. 12-a is a close-up of the mounted clip in the expanded position while FIG. 12-b shows the retracted position. Each one of arms 20' is semi-circular, with an outside diameter approximately equal that of tube 5. The holes in tube 5 act as the pivot points for arms. At. the outside edge of each arm 20' there is a recess 28 to hold tip 11 of clip 3. In the retracted position the arms 20' fold into a circle, overlapping each other. Clip 3 is still resting in recesses 28 of arms 20'. Clearly the semi-circles 20' are also bent towards thread 8, in order to allow them to fold partially over each other, in a manner resembling a four-start thread. The amount of axial forward bending is approximately equal to twice the diameter of the wire used to make actuator 20.

By the way of example, tube 4 is extruded plastic with a diameter of 4 to 8 mm. Actuators 20 are made of stainless steel wire having a diameter of 1.2-1.6 mm. Clip 3 is made of 0.3-0.5 mm thick Nitinol sheet or 0.6-0.9 Nitinol wire, as shown in FIG. 3.

FIG. 13 shows the steps in using the device. It is inserted via catheter 1 as shown in FIG. 13-a. Clip 3 is expanded by rotating ring 24. The expanded arms 20' provide a reference surface to locate the inner wall of tissue 2 without radiological means. Catheter 1 is pulled backwards till arms 20' stop at tissue 2, as shown in FIG. 13-c. Barbs of clip 3 are exposed by rotating disc 27 as shown in FIG. 13-d, and are embedded into tissue 2. In FIG. 13-e, ring 24 is further turned to fold the arms 20' into the retracted position while embedding clip 3 deeper in tissue 2, since rotating disc 24 both folds the arms and pulls on rod 4. After clip 3 is fully embedded in tissue rod 4 is turned to release clip 3 from tool 5. As with the other versions of the invention, the operation is reversible by re-attaching tool to clip. Note that ring 24 is turned to activate tool rather than bushing 21, since clip 3 needs to remain stationary relative to tissue 2 once it is embedded.

While the examples used an elastic clip, it is obvious that the invention can be practiced with a non-elastic deformable clip. By the way of example, the clip shown in FIG. 6 can be made of annealed stainless steel. The installation tools have to be slightly modified to be able to apply both tension and compression to the clip. Such a modification is shown in FIG. 7, wherein arm 16 has a bent tip 16' holding clip 3 from both sides. The clip can be deformed plastically from the shape shown in FIG. 6-a to the shape in FIG. 6-b, embedded in tissue 2 and deformed plastically back to the shape of FIG. 6-a. After that tool 5 is pushed forward to disengage from clip, arms 16 retracted and tool pulled out of catheter 1. The words "clip" and "barb" should be interpreted in a broad sense. Any part left behind in the tissue is considered a clip, regardless of actual shape or material. Any part of the clip used for attachment to the tissue is considered a "barb", regardless of shape, sharpness, material etc. By the way of example, in the context of this invention, an adhesive patch that can be placed over the hole from the inside and pull the hole to close is considered a clip and the adhesive is considered a barb.

What is claimed is:

1. A medical device, comprising:
    an elongated tool having at least one actuator, at least a portion of the at least one actuator proximate a distal end of the elongated tool and receivable through an opening in tissue from a first side of the tissue to a second side of the tissue, the at least one actuator operable from a proximate end of the elongated tool to embed a plurality of tissue piercing tips of a clip from the second side of the tissue to seal the opening in the tissue, each of the plurality of tissue piercing tips of the clip protected after the plurality of tissue piercing tips have been expanded to encompass the opening in the tissue, and the tissue piercing tips unprotected as part of embedding the tissue piercing tips in the tissue.

2. The medical device of claim 1 wherein the elongated tool further comprises:
    an elongated tube having at least one longitudinal passageway extending therethrough; and
    a rod received through the passageway of the elongated flexible tube for rotational and translational movement with respect thereto, the rod having a distal end including an engagement member operable to selectively physically engage and disengage at least a portion of the clip.

3. The medical device of claim 1 wherein the elongated tube has a plurality of longitudinal passageways extending therethrough that each receive a respective one of the plurality of actuators for rotation therein, in addition to the longitudinal passageway that received the rod.

4. The medical device of claim 2 wherein the elongated tool further comprises:
    a sleeve received about the rod to allow rotation and translation of the rod through the sleeve, the sleeve having a plurality of slots, each of the slots of the sleeve sized and dimensioned to engage a respective one of the at least one actuator to selectively rotate the at least one actuator.

5. The medical device of claim 4 wherein rotation of the actuators rotates the piercing tips of the clip into an overlapping relation with adjacent ones of the piercing tips in a retracted configuration.

6. The medical device of claim 5 wherein the elongated tool further comprises:
    a tube extension physically coupled to the tube to move therewith;
    a shaft physically coupled to the tube extension to move therewith;

a ring physically coupled to the shaft to move therewith; and a disc physically coupled to the rod to move therewith, the disc further coupled to transform a rotational motion of the disc into a translational motion of the shaft.

7. The medical device of claim 6 wherein at least one of the disc and the ring includes an inclined surface that transforms the rotational motion of the disc into the translational motion of the shaft.

8. The medical device of claim 6 wherein the proximate end of the rod includes a knob portion to the rod to be grasped and rotated.

9. The medical device of claim 2, further comprising:

the clip having the plurality of resilient tissue piercing tips, the clip further including a stem from which the resilient tissue piercing tips extend, the stem including an engagement member that is complementary to the engagement member of the rod.

10. The medical device of claim 9 wherein the engagement member of the stem is a threaded portion and the engagement member of the rod is a threaded portion.

11. The medical device of claim 9 wherein the stem and the tissue piercing comprise a single unitary structure.

12. The medical device of claim 9 wherein the plurality of tissue piercing tips of the clip are comprised of Nitinol.

13. The medical device of claim 1 wherein each of the at least one actuator has at least one recess to protectively receive a respective one of the tissue piercing tips of the clip prior to embedding of the clip in the tissue.

14. The medical device of claim 2 wherein the tissue piercing tips of the clip embed in the tissue from the second side in response to the rod being pulled.

15. The medical device of claim 9 wherein the engagement member of the rod is configured to selectively detached the clip therefrom after the clip has been embedded in the tissue from the second side and to reattach to the clip thereto after the clip has been detached therefrom.

16. The medical device of claim 15 wherein the tissue piercing tips of the clip are removed from the second side of the tissue in response to the rod being pushed.

17. The medical device of claim 15 wherein the at least one actuator protectively receives the tissue piercing tips of the clip after the clip has been reattached to the engagement member of the rod.

18. The medical device of claim 1 wherein the at least one actuator includes at least three actuators that are configured to provide a tactile feedback through the elongated tool in response to physically contacting the second side of the tissue when the at least three actuators are positioned to embed the tissue piercing tips of the clip in the tissue from the second side.

19. A medical device, comprising:

an elongated tool having a proximate end and a distal end, at least the distal end receivable internally in a body; and at least one actuator having at least one arm located at least proximate the distal end of the elongated tool, which at least one arm protectively retains a respective one of each of a plurality of tissue piercing tips of a clip, used to close a hole in the tissue, until the tissue piercing tips start to pierce the tissue at locations encompassing the hole in the tissue.

20. The medical device of claim 19 wherein at least a portion of the at least one actuator is receivable through the hole to be closed in tissue from a first side of the tissue to a second side of the tissue, the at least one arm of the actuator configured to hold the clip such that the tissue piercing tips face the tissue from the second side when the at least a portion of the at least one actuator is received through the opening from the first side.

21. The medical device of claim 19 wherein the elongated tool comprises an elongated tube having at least one longitudinal passageway extending therethrough and the at least one actuator includes a plurality of actuators each having a respective one of the at least one arm.

* * * * *